(12) United States Patent
Noda et al.

(10) Patent No.: US 11,635,392 B2
(45) Date of Patent: Apr. 25, 2023

(54) RADIATION IMAGING APPARATUS, RADIATION IMAGING METHOD, AND NON-TRANSITORY COMPUTER-READABLE STORAGE MEDIUM

(71) Applicant: CANON KABUSHIKI KAISHA, Tokyo (JP)

(72) Inventors: Takeshi Noda, Kanagawa (JP); Atsushi Iwashita, Tokyo (JP); Sota Torii, Kanagawa (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 335 days.

(21) Appl. No.: 17/091,008

(22) Filed: Nov. 6, 2020

(65) Prior Publication Data

US 2021/0055233 A1 Feb. 25, 2021

Related U.S. Application Data

(63) Continuation of application No. PCT/JP2019/017058, filed on Apr. 22, 2019.

(30) Foreign Application Priority Data

Jun. 7, 2018 (JP) .............................. JP2018-109658

(51) Int. Cl.
  *G01N 23/04* (2018.01)
  *A61B 6/00* (2006.01)
  *G01N 23/20091* (2018.01)

(52) U.S. Cl.
  CPC ........... *G01N 23/04* (2013.01); *A61B 6/4007* (2013.01); *A61B 6/4208* (2013.01); *A61B 6/463* (2013.01);

(Continued)

(58) Field of Classification Search
  CPC ............. G01N 23/04; G01N 23/20091; G01N 2223/401; G01N 2223/423; A61B 6/4007;

(Continued)

(56) References Cited

U.S. PATENT DOCUMENTS 5,115,394 A 5/1992 Walters
5,666,391 A 9/1997 Ohnesorge et al.
(Continued)

FOREIGN PATENT DOCUMENTS

EP 0 782 375 A1 7/1997
JP H06-014911 A 1/1994
(Continued)

OTHER PUBLICATIONS

U.S. Appl. No. 16/103,150, Atsushi Iwashita, filed Aug. 14, 2018.
(Continued)

*Primary Examiner* — Courtney D Thomas
(74) *Attorney, Agent, or Firm* — Venable LLP

(57) ABSTRACT

A radiation imaging apparatus comprises an image generating unit configured to generate a material characteristic image by using a plurality of radiation images of different radiation energy levels; an evaluation information calculation unit configured to calculate evaluation information which indicates a correlation between a plurality of material characteristic images; and a scattered ray amount estimation unit configured to estimate, based on the evaluation information, an amount of scattered rays included in the plurality of radiation images.

20 Claims, 8 Drawing Sheets

(52) U.S. Cl.
CPC ....... *A61B 6/505* (2013.01); *G01N 23/20091* (2013.01); *G01N 2223/401* (2013.01); *G01N 2223/423* (2013.01)

(58) Field of Classification Search
CPC ....... A61B 6/4208; A61B 6/463; A61B 6/505; A61B 6/4233; A61B 6/4241; A61B 6/482; A61B 6/5282; A61B 6/44
See application file for complete search history.

(56) References Cited

U.S. PATENT DOCUMENTS

| | | | |
|---|---|---|---|
| 7,551,716 B2 | 6/2009 | Ruhrnschopf | |
| 3,041,096 A1 | 10/2011 | Bernhardt et al. | |
| 8,355,594 B2 | 1/2013 | Noda et al. | |
| 8,655,034 B2 | 2/2014 | Noda et al. | |
| 8,744,210 B2 | 6/2014 | Noda et al. | |
| 8,923,589 B2 | 12/2014 | Noda et al. | |
| 9,014,450 B2 | 4/2015 | Noda et al. | |
| 9,048,154 B2 | 6/2015 | Takenaka et al. | |
| 9,128,196 B2 | 9/2015 | Sato et al. | |
| 9,134,432 B2 | 9/2015 | Iwashita et al. | |
| 9,234,966 B2 | 1/2016 | Sugawara et al. | |
| 9,423,512 B2 | 8/2016 | Sato et al. | |
| 9,445,030 B2 | 9/2016 | Yagi et al. | |
| 9,462,989 B2 | 10/2016 | Takenaka et al. | |
| 9,468,414 B2 | 10/2016 | Ryu et al. | |
| 9,470,800 B2 | 10/2016 | Iwashita et al. | |
| 9,470,802 B2 | 10/2016 | Okada et al. | |
| 9,541,653 B2 | 1/2017 | Iwashita et al. | |
| 9,655,586 B2 | 5/2017 | Yagi et al. | |
| 9,737,271 B2 | 8/2017 | Iwashita et al. | |
| 9,812,474 B2 | 11/2017 | Yagi et al. | |
| 9,820,713 B2 | 11/2017 | Noda et al. | |
| 9,907,528 B2 * | 3/2018 | Yi | A61B 6/5282 |
| 9,953,414 B2 | 4/2018 | Noda et al. | |
| 9,971,046 B2 | 5/2018 | Ryu et al. | |
| 9,980,685 B2 | 5/2018 | Iwashita et al. | |
| 9,989,656 B2 | 6/2018 | Sato et al. | |
| 10,009,990 B2 | 6/2018 | Takenaka et al. | |
| 10,197,684 B2 | 2/2019 | Terui et al. | |
| 10,274,612 B2 | 4/2019 | Ishii et al. | |
| 10,441,238 B2 | 10/2019 | Terui et al. | |
| 10,779,777 B2 | 9/2020 | Terui et al. | |
| 10,782,251 B2 | 9/2020 | Sato et al. | |
| 2003/0215119 A1 | 11/2003 | Uppaluri | |
| 2008/0013673 A1 | 1/2008 | Ruhmschopf | |
| 2010/0027867 A1 | 2/2010 | Bernhardt | |
| 2014/0239186 A1 | 8/2014 | Sato et al. | |
| 2014/0361189 A1 | 12/2014 | Kameshima et al. | |
| 2016/0270755 A1 | 9/2016 | Takenaka et al. | |
| 2018/0128755 A1 | 5/2018 | Iwashita et al. | |
| 2019/0179036 A1 | 6/2019 | Takenaka et al. | |
| 2019/0320993 A1 | 10/2019 | Noda et al. | |
| 2019/0349541 A1 | 11/2019 | Iwashita et al. | |
| 2020/0124749 A1 | 4/2020 | Takenaka et al. | |
| 2020/0150059 A1 | 5/2020 | Torii et al. | |
| 2020/0150286 A1 | 5/2020 | Terui et al. | |
| 2020/0155097 A1 | 5/2020 | Torii et al. | |
| 2020/0163630 A1 | 5/2020 | Noda et al. | |
| 2020/0211238 A1 | 7/2020 | Iwashita et al. | |
| 2020/0245441 A1 | 7/2020 | Tsukuda et al. | |
| 2021/0041584 A1 | 2/2021 | Terui et al. | |

FOREIGN PATENT DOCUMENTS

| | | |
|---|---|---|
| JP | H09-010199 A3 | 1/1997 |
| JP | 2002-171444 A | 6/2002 |
| JP | 2008-502395 A | 1/2008 |
| JP | 2008-272476 A | 11/2008 |
| WO | 2005/124683 A3 | 12/2005 |

OTHER PUBLICATIONS

U.S. Appl. No. 16/986,841, Asato Kosuge, filed Aug. 6, 2020.
U.S. Appl. No. 17/127,302, Sota Torii, filed Dec. 18, 2020.

* cited by examiner

| MATERIAL | EFFECTIVE ATOMIC NUMBER |
|---|---|
| FAT | 5.9~6.5 |
| WATER | 7.4 |
| MUSCLE | 7.4~7.6 |
| BONE | 12.3~13.8 |

RADIATION IMAGING APPARATUS, RADIATION IMAGING METHOD, AND NON-TRANSITORY COMPUTER-READABLE STORAGE MEDIUM

CROSS-REFERENCE TO RELATED APPLICATIONS

This application is a Continuation of International Patent Application No. PCT/JP2019017058, filed Apr. 22, 2019, which claims the benefit of Japanese Patent Application No. 2018-109658, filed Jun. 7, 2018, both of which are hereby incorporated by reference herein in their entirety.

BACKGROUND OF THE INVENTION

Field of the Invention

The present invention relates to a radiation imaging apparatus, a radiation imaging method, and a non-transitory computer-readable storage medium.

Background Art

A radiation imaging apparatus using a flat panel detector (to be referred to as an "FPD" hereinafter) has become popular as an imaging apparatus to be used for medical image diagnosis by radiation. Since an FPD can perform digital image processing on a captured image, various kinds of applications have been developed and put into practical use. PTL 1 discloses, as one such application, processing by an energy subtraction method.

CITATION LIST

Patent Literature

PTL 1: Japanese Patent Laid-Open No. 2002-171444

If radiation that has been transmitted through an object is scattered inside the object and scattered rays are generated, it may influence the processing by the energy subtraction method unless the amount of scattered rays included in a radiation image is considered.

The present invention has been made in consideration of the above problem and provides a radiation imaging technique that can estimate the amount of scattered rays included in a radiation image.

SUMMARY OF THE INVENTION

A radiation imaging apparatus according to one aspect to the present invention includes the following arrangement. That is, the radiation imaging apparatus is comprising:

a generating unit configured to generate a material characteristic image by using a plurality of radiation images of different radiation energy levels:

a calculation unit configured to calculate evaluation information which indicates a correlation between a plurality of material characteristic images; and an estimation unit configured to estimate, based on the evaluation information, an amount of scattered rays included in the plurality of radiation images.

Further features of the present invention will become apparent from the following description of exemplary embodiments with reference to the attached drawings.

BRIEF DESCRIPTION OF THE DRAWINGS

The accompanying drawings, which are incorporated in and constitute a part of the specification, illustrate embodiments of the invention and, together with the description, serve to explain principles of the invention.

DESCRIPTION OF THE EMBODIMENTS

Embodiments of the present invention will be described in detail below with reference to the accompanying drawings. Note that the constituent elements described in the embodiments are merely examples. The technical scope of the present invention is determined by the scope of the appended claims and is not limited by the individual embodiments to be described below.

First Embodiment

Figure 1:
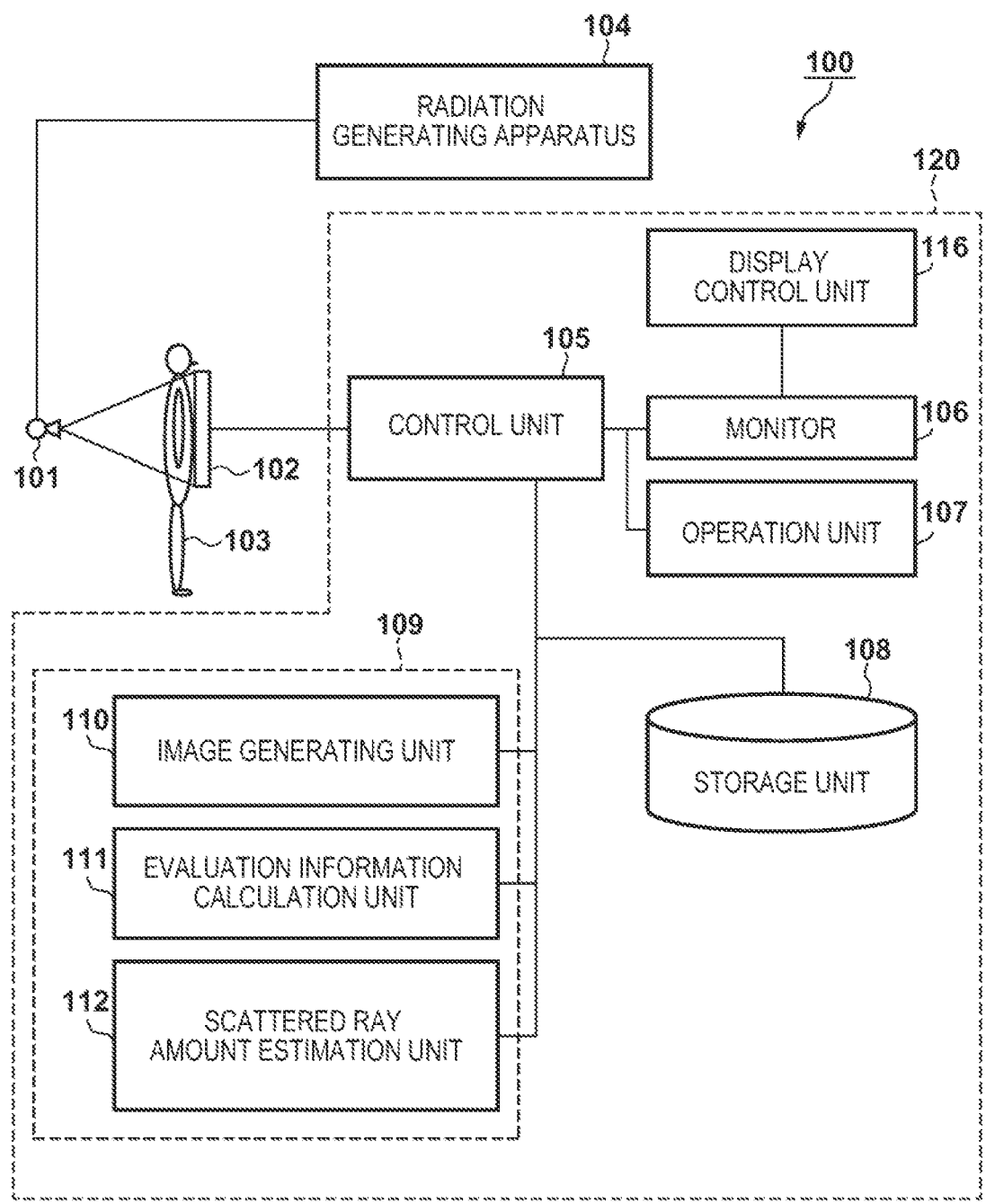
FIG. 1 is a view showing an example of the arrangement of a radiation imaging system according to the first embodiment.

FIG. 1 is a block diagram showing an example of the arrangement of a radiation imaging system 100 according to the first embodiment of the present invention. The radiation imaging system 100 includes a radiation generating apparatus 104, a radiation source 101, an FPD (radiation detection apparatus) 102, and an information processing apparatus 120. Note that the arrangement of the radiation imaging system 100 may also be simply called a radiation imaging apparatus. The information processing apparatus 120 processes information based a radiation image that has captured an object.

The radiation generating apparatus 104 generates radiation by applying a high-voltage pulse to the radiation source 101 when an irradiation switch is pressed, and the radiation source 101 irradiates an object 103 with radiation. Although the type of radiation is not particularly limited, an X-ray can be generally used.

When the object 103 is irradiated with radiation from the radiation source 101, the FPD 102 obtains a radiation image by accumulating charges based on an image signal. The FPD 102 transfers the radiation image to the information processing apparatus 120. Note that the FPD 102 can transfer the radiation image to the information processing apparatus 120 for each imaging operation or can store the captured image in an image storage unit in the FPD 102 without transferring the image for each imaging operation and transfer the stored images all together from the FPD 102 to the information processing apparatus 120 at a predetermined timing. The communication between the FPD 102 and the information processing apparatus 120 may be performed by wired communication or wireless communication.

The FPD 102 includes a radiation detection unit (not shown) in which a pixel array for generating a signal corresponding to the radiation is arranged. The radiation detection unit detects radiation that has been transmitted through the object 103 as image signals. Pixels that output signals corresponding to incident light are arranged in an array (two-dimensional region) in the radiation detection unit. A photoelectric conversion element of each pixel converts radiation that has been converted into visible light by a fluorescent material into an electrical signal, and outputs the converted electrical signal as an image signal. In this manner, the radiation detection unit is configured to detect the radiation that has been transmitted through the object 103 to obtain image signals (radiation image). A driving unit (not shown) of the FPD 102 outputs, to a control unit 105, the image signals (radiation image) read out in accordance with an instruction from the control unit 105.

The control unit 105 includes an image processing unit 109 that processes a radiation image obtained from the FPD 102 and a storage unit 108 that stores the results of image processing operations and various kinds of programs. The storage unit 108 is formed by, for example, a ROM (Read Only Memory), a RAM (Random Access Memory), or the like. The storage unit 108 can store the images output from the control unit 105, the images processed by the image processing unit 109, and the calculation results obtained by the image processing unit 109.

The image processing unit 109 includes, as functional components, an image generating unit 110, an evaluation information calculation unit 111, and a scattered ray amount estimation unit 112. According to these functional components, the function of each unit is implemented by one or a plurality of CPUs (Central Processing Units) using a program loaded from the storage unit 108. The arrangement of each unit of the image processing unit 109 may be formed by an integrated circuit or the like as long as a similar function can be achieved. In addition, it may be formed so that a graphic control unit such as a GPU (Graphics Processing Unit) or the like, a communication unit such as a network card or the like, an input/output control unit such as a keyboard, a display, or a touch panel, and the like will be included as the internal components of the information processing apparatus 120.

A monitor 106 (display unit) displays a radiation image (digital image) received by the control unit 105 from the FPD 102 and an image that has been processed by the image processing unit 109. A display control unit 116 can control the display operation of the monitor 106 (display unit). An operation unit 107 can input instructions to the image processing unit 109 and the FPD 102 and accepts the input of instructions to the FPD 102 via a user interface (not shown).

The control unit 105 uses an energy subtraction method in which new images (for example, a bone image and a soft tissue image) are obtained by processing a plurality of radiation images which are obtained by irradiating an object with different radiation energy levels. In a case in which an imaging operation is to be performed by using the energy subtraction method, at least two radiation images which are captured by different radiation energy levels will be needed to generate one subtraction image. The FPD 102 performs a plurality of sampling operations with respect to one radiation irradiation operation. As a result, the FPD 102 can obtain an image (low-energy radiation image) by low-energy radiation and an image (high-energy radiation image) by high-energy radiation in one radiation irradiation operation. The imaging operation by the FPD 102 may be a still-image capturing operation or a moving-image capturing operation.

Figure 5:
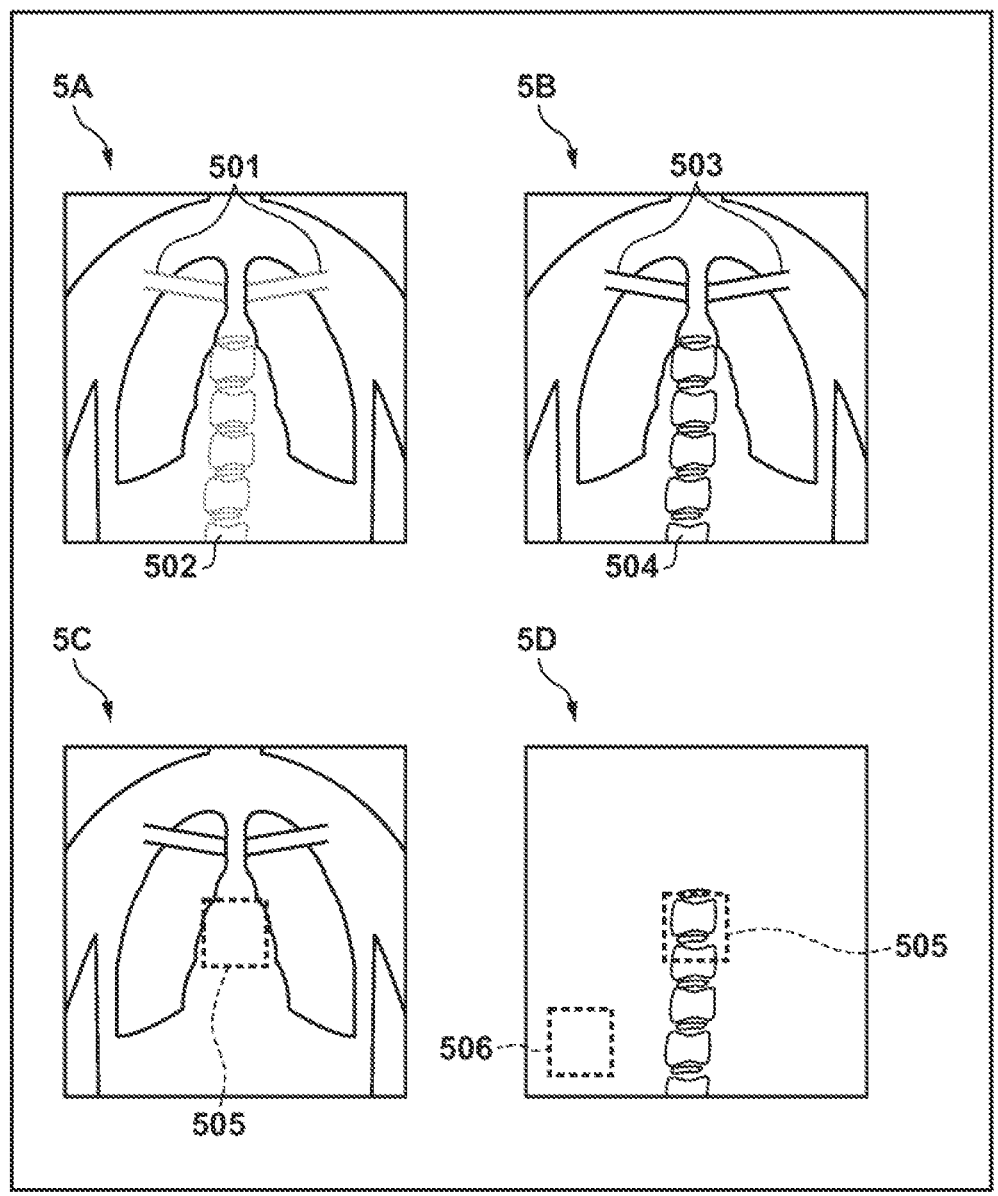
FIG. 5 shows views 5A, 5B, 5C, and 5D which exemplify a high-energy radiation image, a low-energy radiation image, a material separation image of soft tissue, and a material separation image of bone, respectively.

The radiation distribution information temporarily stored in the FPD 102 can be read out after the execution of a sample-and-hold operation, and the control unit 105 reads out radiation distribution information ($X_L$) and radiation distribution information ($X_L+X_H$) from the FPD 102 at different timings. The control unit 105 can obtain radiation distribution information ($X_H$) by subtracting the radiation distribution information ($X_L$) from the radiation distribution information ($X_L+X_H$). In this case, the low-energy radiation distribution information ($X_L$) will be the base image of a low-energy radiation image, and the high-energy radiation distribution information ($X_H$) will be the base image of a high-energy radiation image. Reference numeral 5A of FIG. 5 indicates a view exemplifying a high-energy radiation image, and reference numeral 5B of FIG. 5 indicates a view exemplifying a low-energy radiation image. The contrast of the bone portions (clavicles 503 and vertebrae 504) of the low-energy radiation image in the view 5B of FIG. 5 is clearer than that of the bone portions (clavicles 501 and vertebrae 502) of the high-energy radiation image in the view 5A of FIG. 5.

The image processing unit 109 includes, as functional components, the image generating unit 110, the evaluation information calculation unit 111, and the scattered ray amount estimation unit 112. The image generating unit 110 generates each material characteristic image by using a plurality of radiation images obtained by using different radiation energy levels. That is, the image generating unit 110 generates, from the radiation images captured by the FPD 102, material characteristic images such as an effective atomic number image and material separation images.

An effective atomic number indicates an atomic number corresponding to a case in which an element, a compound, or an element of a mixture is viewed on average, and is a quantitative index that indicates the atomic number of a virtual element which can attenuate photons at the same ratio as this constitutive material. An effective atomic number image refers to an image formed on a pixel basis by an atomic number corresponding to a case in which an object has been represented by a single constitutive material. In addition, material separation images refers to, in a case in which an object is represented by two or more specific materials, images obtained by separating an image into two or more images which are formed based on the thickness or density of the materials.

The evaluation information calculation unit 111 calculates evaluation information that indicates the correlation between a plurality of material characteristic images, and the scattered ray amount estimation unit 112 estimates the amount of scattered rays included in the plurality of radiation images based on the evaluation information.

Figure 2:
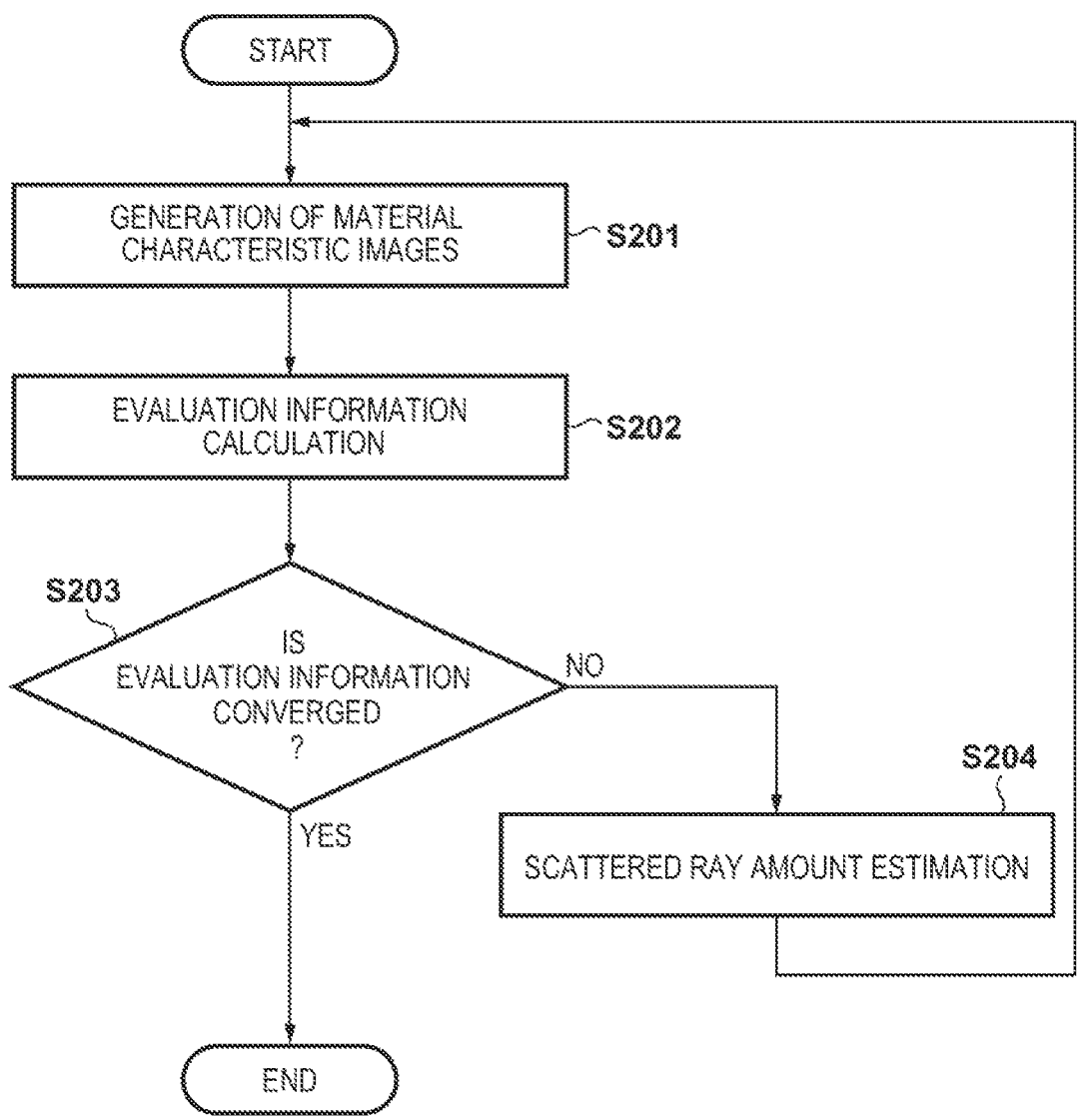
FIG. 2 is a flowchart for explaining the procedure of processing performed in an image processing unit according to the first embodiment.

Processing performed in the image processing unit 109 according to the first embodiment will be described in detail next with reference to the flowchart shown in FIG. 2. The control unit 105 stores each radiation image captured by the FPD 102 in the storage unit 108 and transfers the image to the image processing unit 109.

(Step S201: Generation of Material Characteristic Images)

In step S201, the image generating unit 110 generates, as material characteristic images, an effective atomic number image of each material forming an object or material separation images separated according to respective materials forming the object. The image generating unit 110 generates the material separation images from the high-energy radiation image as shown in view 5A of FIG. 5 and the low-energy radiation image as shown in view 5B of FIG. 5 captured by the FPD 102 based on the following equations (1) and (2).

$$-\ln X_L = \mu_{LA} d_A + \mu_{LB} d_B \qquad (1)$$

$$-\ln X_H = \mu_{HA} d_A + \mu_{HB} d_B \qquad (2)$$

Here, $X_L$ represents the low-energy radiation distribution information, and the low-energy radiation distribution information ($X_L$) becomes the base image of the low-energy radiation image. Also, $X_H$ represents the high-energy radiation distribution information $X_H$, and the high-energy radiation distribution information ($X_H$) becomes the base image of the high-energy radiation image. A low-energy radiation image will be referred to as a low-energy radiation image $X_L$, and a high-energy radiation image will be referred to as a high-energy radiation image $X_H$ hereinafter.

μ represents a ray attenuation coefficient, and d represents the thickness of a material. Suffixes H and L represent high energy and low energy, respectively, and suffixes A and B represent materials (for example, soft tissue and bone, respectively) to be separated. Note that although the soft tissue and the bone are used here as examples of materials to be separated, the present invention is not limited to these materials, and arbitrary materials can be used.

In this embodiment, the control unit 105 functions as an obtainment unit which obtains the plurality of radiation images ($X_L$ and $X_H$) captured by the FPD 102 (radiation detection apparatus) by a single radiation irradiation operation from the radiation source 101. The control unit 105 (the obtainment unit) obtains the plurality of radiation images, which have been captured by the FPD 102 (radiation detection apparatus), as a plurality of radiation images obtained by using different radiation energy levels. The image generating unit 110 generates a plurality of material characteristic images based on the plurality of radiation images ($X_L$ and $X_H$) obtained by the control unit 105 (obtainment unit).

The image generating unit 110 can obtain the following equation (3) by performing arithmetic processing to solve the simultaneous equations formed by equations (1) and (2), and obtain the material separation images which are separated according to the respective materials. Reference numeral 5C of FIG. 5 indicates a view exemplifying a material separation image obtained based on a thickness $d_A$ of the soft tissue of equation (3), and reference numeral 5D of FIG. 5 indicates a view exemplifying a material separation image obtained based on a thickness do of the bone of equation (3).

$$d_A = \frac{1}{\mu_{LA}\mu_{HB} - \mu_{LB}\mu_{HA}} (\mu_{LB}\ln X_H - \mu_{HB}\ln X_L) \qquad (3)$$

$$d_R = \frac{1}{\mu_{LR}\mu_{HR} - \mu_{RB}\mu_{LA}} (\mu_{LA}\ln X_H - \mu_{HA}\ln X_L)$$

Figures 3, 4:
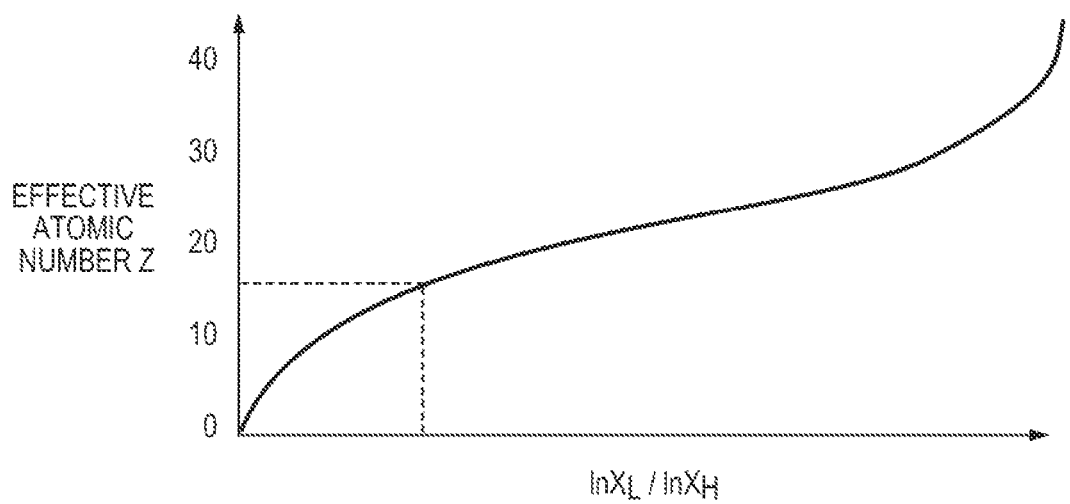
FIG. 3 is a graph showing the relationship between an effective atomic number and a logarithmic ratio between low-energy radiation distribution information and high-energy radiation distribution information.
FIG. 4 is a table showing an example of the effective atomic numbers of materials.

Also, the image generating unit 110 can obtain a logarithmic ratio ($\ln X_L / \ln X_H$) between the low-energy radiation distribution information ($X_L$) and the high-energy radiation distribution information ($X_H$), and generate an effective atomic number image $Z_{eff}$ based on the obtained logarithmic ratio. FIG. 3 is a view showing the relationship between an effective atomic number Z and the logarithmic ratio of the low-energy radiation distribution information and the high-energy radiation distribution information. The relationship between the effective atomic number Z and the logarithmic ratio as shown in FIG. 3 can be made into a table in advance, and the image generating unit 110 can refer to the table to generate the effective atomic number image Zr by specifying the effective atomic number Z corresponding to the logarithmic ratio.

FIG. 4 is a table showing an example of the effective atomic numbers of materials. For example, the effective atomic number of fat is 5.9 to 6.5, and the effective atomic number of water is 7.4. Also, the effective atomic number of muscle is 7.4 to 7.6, and the effective atomic number of bone is 12.3 to 13.8. In this manner, a specific region forming the human body (object) such as fat, water, muscle, bone, or the like can be specified by using the effective atomic number.

(Step S202: Evaluation Information Calculation)

In step S202, the evaluation information calculation unit 111 calculates the evaluation information indicating the correlation between the plurality of material characteristic images (for example, the material separation images). In general, the materials separated by the material separation operation tend to be materials that have different properties. For example, materials such as bone and fat, fat and a contrast agent, and the like, which are materials with different properties from each other, tend to show high independence and low correlation. As the evaluation information that indicates the correlation of the plurality of material characteristic images, for example, mutual information, information entropy, SAD (Sum of Absolute Differences), sum of squared differences, a correlation coefficient (normalized cross-correlation), or the like can be used.

The evaluation information calculation unit 111 can calculate one of mutual information, information entropy, SAD, and the sum of squared differences as the evaluation information indicating the correlation of the plurality of material characteristic images.

In a case in which mutual information, information entropy, SAD, or the sum of squared differences is to be used as the evaluation information that indicates the correlation of the plurality of material characteristic images, a parameter that maximizes the error between the images, that is, a parameter that maximizes the evaluation information based on an evaluation function can be obtained. In a case in which the evaluation information calculation unit 111 is to calculate one of mutual information, information entropy, SAD, and the sum of squared differences as the evaluation information, the scattered ray amount estimation unit 112 will estimate the amount of scattered rays at which the calculation result becomes maximum to be the amount of scattered rays included in each of the plurality of radiation images.

The evaluation information calculation unit 111 can calculate, as the evaluation information, a correlation coefficient that indicates the correlation of the plurality of material characteristic images.

In a case in which a correlation coefficient is to be used as the evaluation information that indicates the correlation of the plurality of material characteristic images, a parameter that minimizes the degree of correlation between the images, that is, a parameter that minimizes the absolute value of the evaluation information can be obtained. In a case in which the evaluation information calculation unit 111 is to calculate the correlation coefficient as the evaluation information, the scattered ray amount estimation unit 112 will estimate an amount of scattered rays at which the absolute value of the correlation coefficient becomes minimum as the amount of scattered rays included in each of the plurality of radiation images.

This embodiment employs a correlation coefficient (normalized cross-correlation) as the evaluation information, and the evaluation information calculation unit 111 calculates a correlation coefficient ZNCC based on an evaluation function of equation (4) as follows. By using the correlation coefficient (normalized cross-correlation) as the evaluation information, the evaluation information that indicates the correlation between the material characteristic images can be obtained without depending on the size of the pixel value of each material characteristic image.

$$ZNCC = \frac{\sum_{x,y}(d_A(x,y)-\mu_A)(d_B(x,y)-\mu_B)}{\sqrt{\sum_{x,y}(d_A(x,y)-\mu_A)^2 \sum_{x,y}(d_B(x,y)-\mu_B)^2}} \quad (4)$$

In equation (4), Σ represents the total sum of the pixel information within a region of interest of the material characteristic images. That is, Σ represents the total sum of the pixel information within the region of interest of the material separation images obtained by decomposing the object into a plurality of materials. For example, if the decomposed materials are soft tissue and bone, the total sum of pixel information within a region of interest of a material separation image obtained based on the thickness $d_A$ of the soft tissue and a material separation image obtained based on the thickness $d_B$ of the bone will be indicated.

In addition, sa represents an average of the pixel information within a region of interest of the material separation image of the soft tissue, and μb represents the pixel information within a region of interest of the material separation image of the bone. This region of interest can be set by designating, from an external operation unit, a region of high interest for the operator where the materials to be separated are both present as shown by a region 505 in view 5C of FIG. 5 and view 5D of FIG. 5. Also, a portion corresponding to a specific part of the object to be captured may be set as the region of interest. Furthermore, a region where the features of the materials to be separated are more easily apparent may also be selected as the region of interest.

(Step S203: Evaluation Information Convergence Determination)

In step S203, the evaluation information calculation unit 111 determines whether the evaluation information obtained in step S202 has converged. The evaluation information calculation unit 111 stores the evaluation information which was obtained in the first calculation operation in the storage unit 108. Subsequently, the evaluation information calculation unit 111 performs convergence determination of the evaluation information obtained by the second or subsequent repetitive calculation operation.

The evaluation information calculation unit 111 compares, for example, the evaluation information obtained by an (n+1)th (n is an integer equal to or more than 1) repetitive calculation and the evaluation information based on an nth calculation stored in the storage unit 108. More specifically, the evaluation information obtained in the second repetitive calculation and the evaluation information based on the first calculation stored in the storage unit 108 are compared. Alternatively, the evaluation information obtained in the third repetitive calculation and the evaluation information based on the second calculation stored in the storage unit 108 are compared.

A predetermined operation count may be set or the point of time at which the correlation coefficient ZNCC of equation (4) stops changing due to the repetitive calculation may be set for the convergence determination. For example, in a case in which the difference between the pieces of the evaluation information obtained as a comparison result or the change ratio of the evaluation information becomes equal to or less than a reference value of the convergence determination, the evaluation information calculation unit 111 will determine that the evaluation information has converged (YES in step S203) and end the processing.

If it is determined that the evaluation information has converged (YES in step S203) when the evaluation information calculation unit 111 determines whether the evaluation information obtained by the repetitive calculation operations has converged, the scattered ray amount estimation unit 112 will estimate that the amount of scattered rays used in the calculation of the converged evaluation information is the amount of scattered rays included in each of the plurality of radiation images.

On the other hand, if it is determined that the evaluation information has not converged in the convergence determination of step S203 (NO in step S203), the evaluation information calculation unit 111 will advance the process to step S204. Subsequently, each amount of scattered rays is estimated in the following step S204, and the processes of steps S201 and S202 are repeated and executed by taking into account each estimated amount of scattered rays.

(Step S204: Scattered Ray Amount Estimation)

In step S204, the scattered ray amount estimation unit 112 estimates the amount of scattered rays included in the high-energy radiation image $X_H$ and that included in the low-energy radiation image $X_L$. The estimation of each amount of scattered rays is performed as follows. First, equations (1) and (2) are changed into equations (5) and (6) as follows by letting $S_H$ be the amount of scattered rays included in the high-energy radiation image $X_H$ and $S_L$ be the amount of scattered rays included in the low-energy radiation image $X_L$.

The scattered ray amount estimation unit 112 generate pieces of image information ($X_L-S_L$ and $X_H-S_H$) by subtracting each set amount of scattered rays from the corresponding one of the radiation images ($X_H$ and $X_L$). The evaluation information calculation unit 111 calculates the evaluation information ZNCC by repetitive calculation based on each of the pieces of the image information ($X_L-S_L$ and $X_H-S_H$).

$$-\ln(X_L-S_L)=\mu_{LA}d_A+\mu_{LB}d_B \quad (5)$$

$$-\ln(X_H-S_H)=\mu_{HA}d_A+\mu_{HB}d_B \quad (6)$$

in equation (5), $X_L-S_L$ on the left-hand side represents the low-energy radiation image (image information) obtained by subtracting the amount $S_L$ of scattered rays from the low-energy radiation image $X_L$, and in equation (6), $X_H-S_H$ represents the high-energy radiation image (image information) obtained by subtracting the amount $S_H$ of scattered rays from the high-energy radiation image $X_H$.

The scattered ray amount estimation unit 112 generates each piece of image information by changing the setting of each amount of scattered rays, and the evaluation information calculation unit 111 repetitively calculates the evaluation information based on each piece of image information generated by changing the setting of each amount of scattered rays.

In this case, since the amounts $S_H$ and $S_L$ of scattered rays are pieces of unknown information, the scattered ray amount estimation unit 112 will set an initial value of the amount of scattered rays and obtain an optimal value based on the evaluation function of equation (4) while minutely changing the setting of the initial value. Various kinds of non-linear optimization methods, for example, the bisection method, the gradient method, the Newton's method, and the like can be used as the optimization method.

The four pieces of unknown information are the thicknesses (for example, the thickness $d_A$ of the soft tissue and the thickness $d_B$ of the bone) of the plurality of materials to be separated, the amount $S_H$ of scattered rays of the high-energy radiation image $X_H$, and the amount $S_L$ of scattered rays of the low-energy radiation image $X_L$. To obtain these four pieces of unknown information, the scattered ray amount estimation unit 112 can analyze the unknown information by setting another constraint to the three equations (4), (5), and (6).

As a constraint, it is possible to add a constraint that sets the thickness $d_B$ of the bone to 0 at a portion, for example, an abdominal portion or the like, where an analysis target material (for example, the bone) is obviously not included in the object, as shown in a region 506 of view 5D of FIG. 5. Also, a reference material whose thickness information is already known may be arranged in a portion without the object, and a constraint that sets the analysis result of thickness of the reference material to be the known thickness value may be added.

In addition, in a case in which the ratio of the amount of scattered rays in the high-energy radiation image $X_H$ and the amount of scattered rays in the low-energy radiation image $X_L$ is known in advance, the relationship between the amounts of scattered rays may be set as $S_H = \alpha S_L$ by setting the ratio as a to associate the amount $S_H$ of scattered rays of the high-energy radiation image $X_H$ and the amount $S_L$ of scattered rays of the low-energy radiation image $X_L$. Since this will establish a constant relationship between $S_H$ and $S_L$, obtaining the optimal value of one amount of scattered rays will allow the optimal value of the other amount of scattered rays to be obtained.

For example, the amount $S_H$ of scattered rays of the high-energy radiation image $X_H$ can be minutely changed as one amount of scattered rays, and the process may return to the process of step S201 to obtain the thicknesses (for example, the thickness $d_A$ of the soft tissue and the thickness $d_B$ of the bone) of the analysis target materials from equations (5) and (6). Subsequently, in the process of step S202, the evaluation information calculation unit 111 can obtain the evaluation information indicating the correlation between the plurality of material characteristic images (for example, the material separation images) based on the correlation coefficient ZNCC of equation (4).

By repeating the processes of steps S204, S201, and S202, the evaluation information calculation unit 111 obtains the optimal value at which the correlation coefficient ZNCC of equation (4) converges. In a case in which the correlation coefficient of equation (4) is to be used as the evaluation function, the information of the amount of scattered rays at which the evaluation function ZNCC is minimized is obtained by, for example, an optimization method such as the bisection method, the gradient method, the Newton's method, or the like. That is, the evaluation information calculation unit 111 obtains the amount $S_H$ of scattered rays of the high-energy radiation image $X_H$ and the amount $S_L$ of scattered rays of the low-energy radiation image $X_L$ by repetitive calculation so as to minimize the evaluation function ZNCC.

By repeating the processes of steps S201 and S202 from step S204, the amounts $S_H$ and $S_L$ of scattered rays can be estimated, and the thicknesses (the thickness $d_A$ of the soft tissue and the thickness $d_B$ of the bone) of the materials can be obtained based on a result obtained by removing the amounts of scattered rays from the plurality of radiation images of different energy levels.

Each material separation image first obtained in the process of step S201 will be an image set in a state including the amount of scattered rays. However, by estimating (step S204) the amounts ($S_H$ and $S_L$) of scattered rays of a plurality of radiation images ($X_L$ and $X_H$) of different energy levels, obtaining (step S201) the thicknesses (the thickness $d_A$ of the soft tissue and the thickness $d_B$ of the bone) of analysis target materials based on equations (5) and (6), and obtaining (YES in steps S202 and S203) the amounts ($S_H$ and $S_L$) of scattered rays so as to minimize the evaluation function of equation (4), the thicknesses (the thickness $d_A$ of the soft tissue and the thickness d of the bone) of the respective materials that have been separated can be obtained, by using the relationship of equation (7) as follows, based on the result obtained by subtracting the amounts of scattered rays from the plurality of radiation images of different energy levels, and the material separation images separated according to the respective materials can be obtained.

Based on the final estimated amounts of scattered rays as shown in equation (7) below, the image generating unit 110 generates each material separation image with the corrected thickness of the material. Here, in equation (7), $X_L$–$S_L$ represents a low-energy radiation image (image information) obtained by subtracting the amount S; of scattered rays from the low-energy radiation image $X_L$, and $X_H$–$S_H$ represents a high-energy radiation image (image information) obtained by subtracting the amount $S_H$ of scattered rays from the high-energy radiation image $X_H$.

$$d_A = \frac{1}{\mu_{LA}\mu_{HB} - \mu_{LB}\mu_{HA}} (\mu_{LB}\ln(X_H - S_H) - \mu_{HB}\ln(X_L - S_L)) \quad (7)$$

$$d_B = \frac{1}{\mu_{LB}\mu_{HA} - \mu_{HB}\mu_{LA}} (\mu_{LA}\ln(X_H - S_H) - \mu_{HA}\ln(X_L - S_L))$$

The monitor 106 (display unit) displays each radiation image (digital image) received by the control unit 105 from the FPD 102 and each image which has undergone image processing by the image processing unit 109. The display control unit 116 causes the monitor 106 (display unit) to display each captured radiation image. That is, the display control unit 116 performs display control to cause the monitor 106 (display unit) to display each radiation image (digital image) received by the control unit 105 from the FPD 102 and each image which has undergone image processing by the image processing unit 109.

For example, the display control unit 116 can perform display control to combine the radiation images ($X_H$ and $X_L$) including the respective amounts of scattered rays, the radiation images ($X_H$–$S_H$ and $X_L$–$S_L$) obtained by subtracting the amounts of scattered rays from the respective radiation images, and the material separation images based on the thicknesses ($d_A$ and $d_B$) of the respective separated materials, and cause monitor 106 (display unit) to display the combined images.

The display control unit 116 can also perform display control to cause the display unit to display at least one image selected by the operator from the images displayed on the monitor 106 (display unit).

Figure 6:
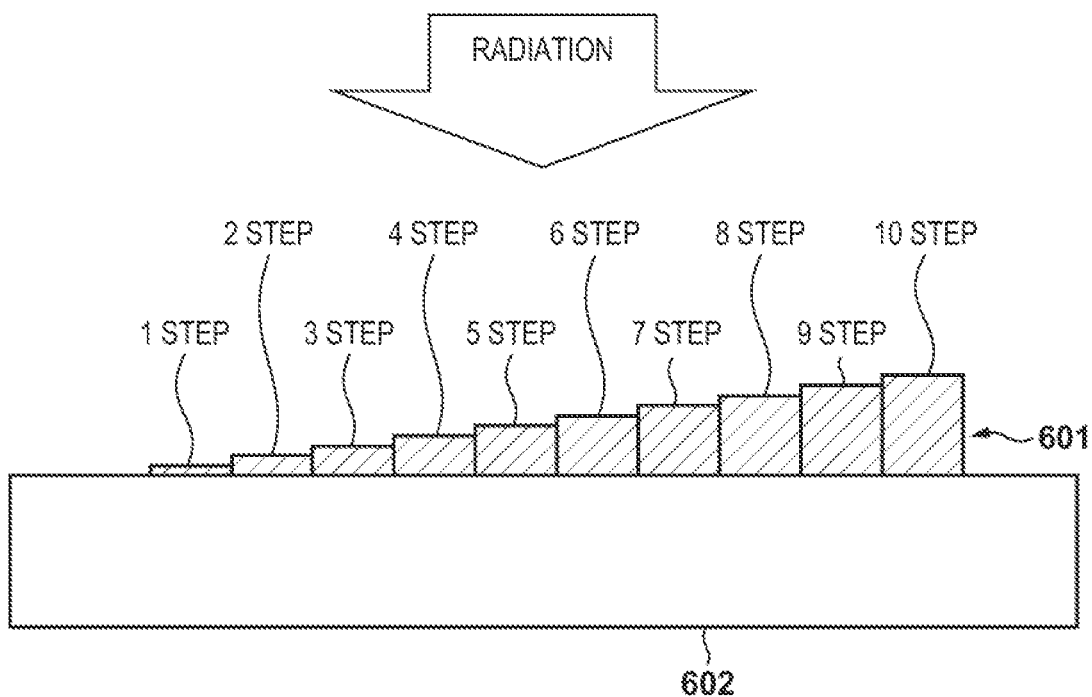
FIG. 6 is a view showing an example of the member arrangement of an imaging experiment applying the processing according to the first embodiment.

FIG. 6 is a view showing the member arrangement of an imaging experiment applying the processing according to the first embodiment. A member 601 which is formed stepwise is a member corresponding to the bone and is formed by aluminum. The member 601 has ten steps, and the thickness (height) of each step is already known. A member 602 is an acrylic plate corresponding to the soft tissue, and the thickness (height) of the acrylic plate is already known. In the imaging experiment, radiation is emitted from the upper side of the member 601 to capture the high-energy radiation image $X_H$ and the low-energy radiation image $X_L$, and material separation is performed by applying the processing according to this embodiment to obtain the thickness of each material by removing the corresponding amount of scattered rays.

Figure 7:
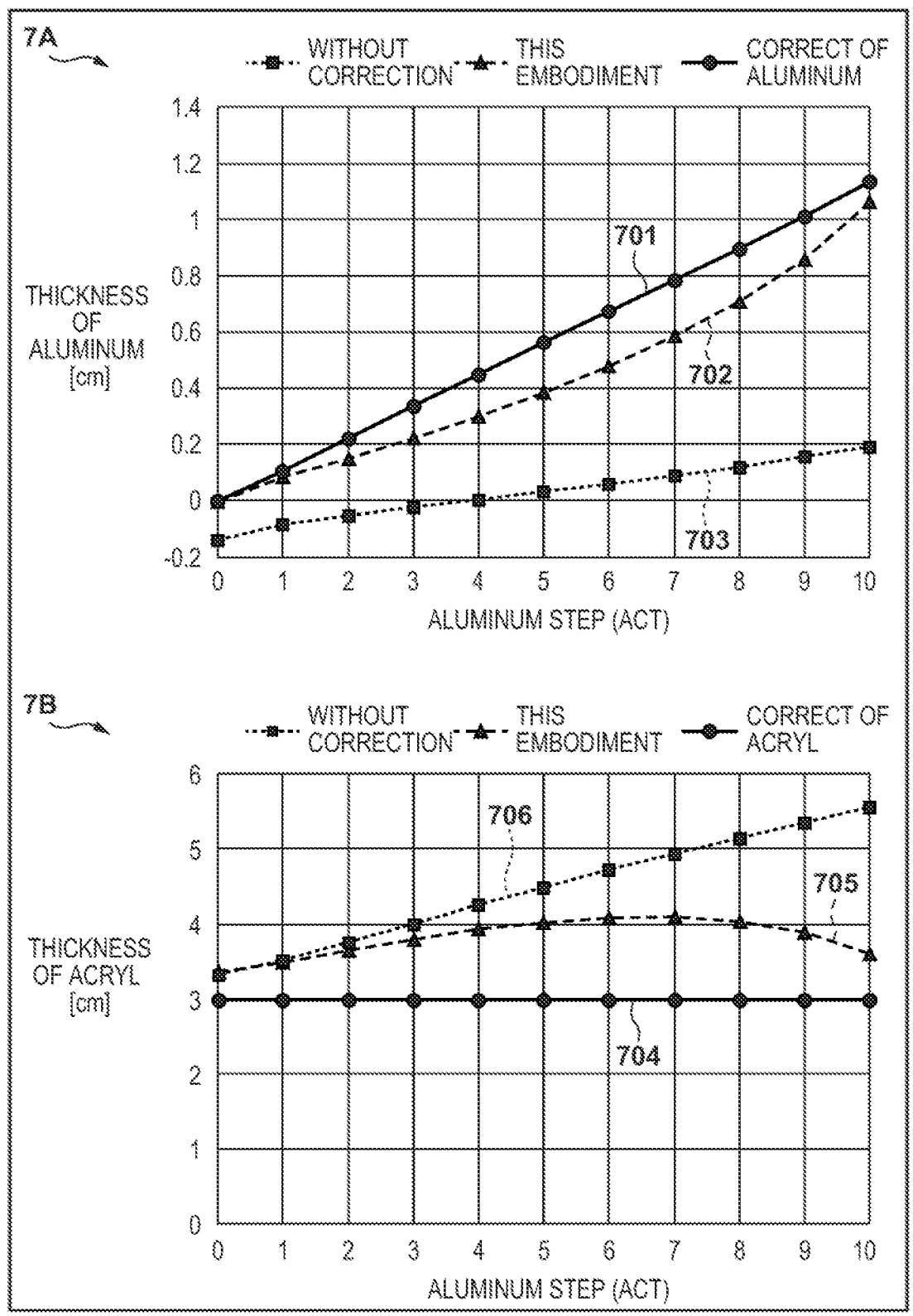
FIG. 7 is a view showing the results of the imaging experiment according to the first embodiment.

FIG. 7 is a view showing the results of the imaging experiment according to the first embodiment. Reference numeral 7A of FIG. 7 is a chart showing the measurement results of the thickness of the aluminum member. The ordinate indicates the thickness of the aluminum member, and the abscissa indicates the number of steps of the aluminum member. The aluminum member has ten steps, and a waveform 701 showing the correct thickness of the aluminum member is indicated by a straight line rising to the right. A waveform 702 shows an experiment result in which the thickness of the aluminum member was obtained based on a result obtained by removing the amounts of scattered rays by using the processing according to the first embodiment. A waveform 703 shows an experiment result in which the thickness of the aluminum member was obtained based on processing performed without applying the processing according to the first embodiment (processing (without correction) performed in a state including the amounts of scattered rays).

Compared to the fact that the thickness of the aluminum member is greatly underestimated compared to the waveform 701 indicating the correct thickness of the aluminum member in the processing (waveform 703) performed without the application of the processing according to the embodiment, a value quantitatively close to the waveform 701 indicating the correct thickness of the aluminum member is obtained by the processing (waveform 702) according to this embodiment.

Reference numeral 7B of FIG. 7 is a chart showing the measurement results of the thickness of the acrylic plate. The ordinate indicates the thickness of the acrylic plate, and the abscissa indicates the number of the steps of the aluminum member. The aluminum member hasten steps. Although the height of each step of the aluminum member changes in accordance with the number of the steps, the thickness of the acrylic plate is constant. A waveform 704 showing the correct thickness of the acrylic plate is a straight line indicating a constant thickness. A waveform 705 shows an experiment result in which the thickness of the acrylic plate was obtained based on a result obtained by removing the amounts of scattered rays by using the processing according to this embodiment. A waveform 706 shows an experiment result in which the thickness of the acrylic plate was obtained based on processing performed without applying the processing according to this embodiment (processing (without correction) performed in a state including the amounts of scattered rays).

Compared to the fact that the thickness of the acrylic plate is overestimated compared to the waveform 704 indicating the correct thickness of the acrylic plate in the processing (waveform 706) performed without the application of the processing according to the embodiment, a value close to that of the waveform 704 indicating the correct thickness of the acrylic plate is obtained by the processing (waveform 705) according to this embodiment.

According to this embodiment, more suitable material separation images can be provided while estimating the amount of scattered rays of the high-energy radiation image $X_H$ and the amount of scattered rays of the low-energy radiation image $X_L$ in the manner shown in charts 7A and 7B of FIG. 7. That is, the thickness of each separated material can be obtained based on the result obtained by removing each amount of scattered rays from the corresponding one of the plurality of radiation images ($X_H$ and $X_L$), and the material separation images separated according to the respective materials can be obtained.

According to this embodiment, as an arrangement for detecting radiation of different energy levels, the amount of scattered rays from each of the plurality of radiation images with different energy distributions can be accurately estimated without using a plurality of cumulative fluorescent material sheets, and the amount of scattered rays can be removed from each of these plurality of images.

In addition, the influence of the amount of scattered rays included in each radiation image increases when the difference between a high-energy radiation image and a low-energy radiation image is small. However, according to this embodiment, material separation can be performed by accurately estimating the amount of scattered rays of the radiation image obtained in one shot of energy subtraction imaging.

Second Embodiment

The first embodiment described a case in which the distribution of the amount of scattered rays becomes constant regardless of the pixel position. However, this embodiment will describe an arrangement that improves the estimation accuracy of the amount of scattered rays by taking into account, as the distribution characteristic of the amount of scattered rays, pixel value dependence, positional dependence, or object imaging part dependence.

In the following description, a description of pans similar to those of the first embodiment will be omitted to avoid redundancy, and only the component parts specific to the second embodiment will be described. In the arrangement according to this embodiment, the amount of scattered rays can be appropriately estimated even in a case in which the distribution characteristic of the amount of scattered rays has spatial dependence.

The first embodiment assumes that the amount of scattered rays will have a constant value regardless of the pixel position as represented by amounts $S_H$ and $S_L$ of scattered rays of equations (5) and (6), respectively. However, since the shape of the object is not uniform in general, the amount of scattered rays will also have a distribution shape.

Since scattered rays are rays of radiation that are generated when the rays are scattered inside a material, the scattered rays will not be generated when the rays are not transmitted through a material. Also, the scattered rays cannot be transmitted in a case in which a material is so thick that the radiation cannot be transmitted. Hence, a function that has a distribution shape (convex shape) in which the amount of scattered rays increases in accordance with the radiation dose can be used.

Figure 8:
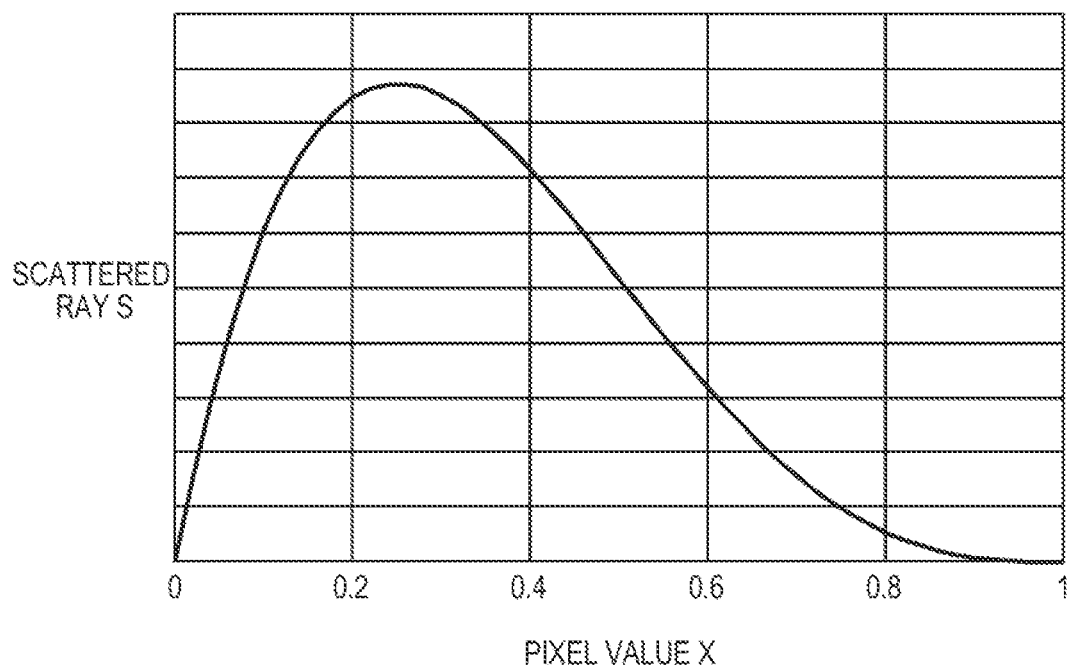
FIG. 8 is a graph representing the distribution shape of the amount of scattered rays by a function that has pixel value dependence.

Letting X be the pixel value of a captured radiation image, an amount S of scattered rays can be expressed by a beta function that has pixel value dependence in the manner of, for example, equation (8) as follows. FIG. 8 is a graph representing the distribution characteristic (distribution shape) of the amount of scattered rays by a beta function which has pixel value dependence. In FIG. 8, the abscissa indicates the pixel value, and the ordinate indicates the amount S of scattered rays.

$$S(X)=X^{\alpha-1}(1-X)^{\beta-1} \qquad (8)$$

In equation (8), α and β are parameters. Although a beta function will be exemplified as a function that indicates the distribution shape of the amount of scattered rays in the second embodiment, the present invention is not limited to this and another function such as a Gaussian distribution, X log X, or the like. That is, the scattered ray amount estimation unit 112 will use the function (equation (8)) which has pixel value dependence to represent the distribution shape of the amount of scattered rays, and generate each piece of image information ($X_L$–$S(X)_L$ and $X_H$–$S(X)_H$) which is obtained by subtracting, from each radiation image, the corresponding amount of scattered rays represented by a function such as equation (8).

Also, a spatial frequency distribution such as a blur or the like can be considered as a distribution characteristic (distribution shape) of the amount of scattered rays. In this case, the distribution shape of the amount of scattered rays can be represented by a function with positional dependence in the manner of equation (9) as follows. That is, the scattered ray amount estimation unit 112 will use the function (equation (9)) which has positional dependence to represent the distribution shape of the amount of scattered rays, and generate each piece of image information ($X_L$–$S(X)_L$ and $X_H$–$S(X)_H$) which is obtained by subtracting, from each radiation image, the corresponding amount of scattered rays represented by a function such as equation (9).

$$S(X)=X^{\alpha-1}(1-X)^{\beta-1}*C(x,y) \qquad (9)$$

in equation (9), α and β are parameters in a similar manner to equation (8). G(x,y) represents the convolution of a blur kernel using a Gaussian function or the like, and equation (9) can be used to represent the generation of a blur due to the scattering of scattered rays inside an object. For example, by setting a blur kernel so as to increase the weight as the position gets closer to the position of a pixel of interest and to decrease the weight as the position gets farther from the position of the pixel of interest, the distribution shape of the amount of scattered rays can be represented by a function with positional dependence.

Since the shape of an object is not uniform, the amount of scattered rays will also have a different shape depending on the imaging part of the object. Hence, in equations (8) and (9), the setting of the parameters and the blur kernel of the function representing the distribution shape of the amount of scattered rays can be changed in accordance with the imaging part of the object. By changing the setting of the parameters and the blur kernel in accordance with the imaging part of the object in this manner, the distribution shape of the amount of scattered rays can be represented by a function with imaging part dependence.

For example, the scattered ray amount estimation unit 112 will use a function which has object imaging part dependence to represent the distribution shape of the amount of scattered rays, and generate each piece of image information ($X_L$–$S(X)_L$ and $X_H$–$S(X)_H$) which is obtained by subtracting, from each radiation image, the corresponding amount of scattered rays represented by the function which has imaging part dependence. The evaluation information calculation unit 111 will calculate the evaluation information (equation (4)) based on the pieces of image information ($X_L$–$S(X)_L$ and $X_H$–$S(X)_H$), and repetitively calculate the evaluation information based on the image information generated by an amount of scattered rays in which a value of a function (S(x)) has changed.

The processing according to this embodiment can be executed by substituting $S_L$ and $S_H$ of equations (5) and (6), respectively, with equation (8) or equation (9), and other procedures of the processing are similar to those of the first embodiment. As an example of a case in which the distribution shape of the amount of scattered rays is represented by equation (8), the results of a material separation imaging experiment using a member arrangement similar to that of FIG. 6 are shown in FIG. 9.

Figure 9:
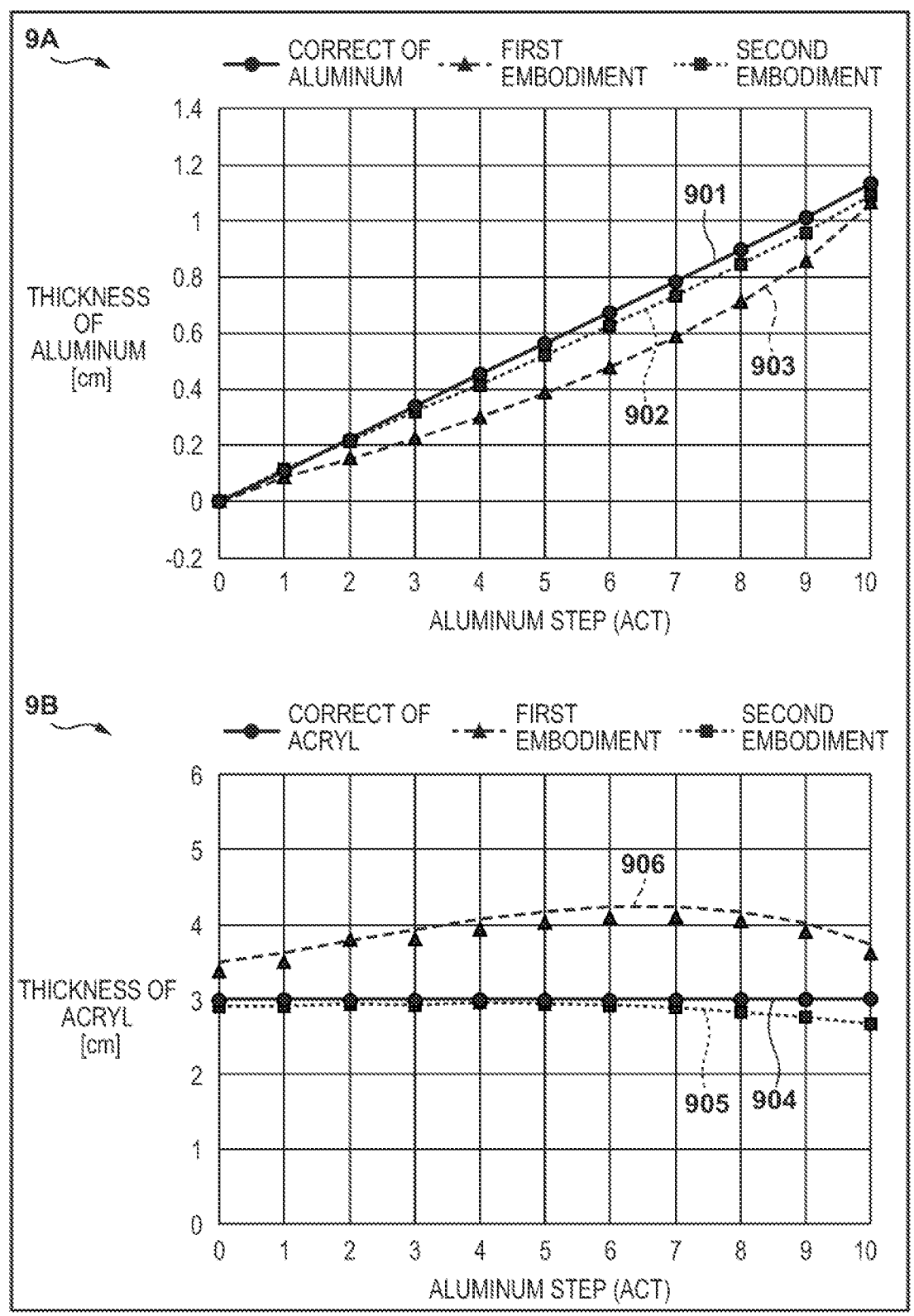
FIG. 9 is a view showing the results of an imaging experiment according to second embodiment.

FIG. 9 is a view showing the results of the imaging experiment according to the second embodiment. Reference numeral 9A of FIG. 9 is a chart showing the measurement results of the thickness of an aluminum member. The ordinate indicates the thickness of the aluminum member, and the abscissa indicates the number of steps of the aluminum member. In a similar manner to the imaging experiment described in the first embodiment, the aluminum member has ten steps, and a waveform 901 showing the correct thickness of the aluminum member is indicated by a straight line rising to the right. A waveform 902 shows an experiment result in which the thickness of the aluminum member was obtained based on a result obtained by removing the amounts of scattered rays by using the processing according to the second embodiment. A waveform 903 shows an experiment result in which the thickness of the aluminum member was obtained based on a result obtained by removing the amounts of scattered rays by using the processing according to the first embodiment.

Compared to the processing (waveform 903) according to the first embodiment, the processing (waveform 902) according to the second embodiment can obtain a value quantitatively closer to the waveform 901 which shows the correct thickness of the aluminum member.

Reference numeral 9B of FIG. 9 is a chart showing the measurement results of the thickness of the acrylic plate. The ordinate indicates the thickness of the acrylic plate, and the abscissa indicates the number of the steps of the aluminum member. The aluminum member has ten steps. Although the height of each step of the aluminum member changes in accordance with the number of the steps, the thickness of the acrylic plate is constant. A waveform 904 showing the correct thickness of the acrylic plate is a straight line indicating a constant thickness. A waveform 905 shows an experiment result in which the thickness of the acrylic plate was obtained based on a result obtained by removing the amounts of scattered rays by using the processing according to the second embodiment. A waveform 906 shows an experiment result in which the thickness of the acrylic plate was obtained based on a result obtained by removing the amounts of scattered rays by using the processing according to the first embodiment.

Compared to the processing (waveform 906) according to the first embodiment, the processing (waveform 905) according to the second embodiment can obtain a value quantitatively closer to the waveform 904 which shows the correct thickness of the acrylic plate.

According to this embodiment, the amount of scattered rays can be estimated with higher accuracy by using a function that considers the distribution shape of the amount of scattered rays.

In this manner, according to the present invention, more suitable material separation images can be provided while estimating the amount of scattered rays of the high-energy radiation image $X_H$ and the amount of scattered rays of the low-energy radiation image $X_L$.

According to the present invention, the amount of scattered rays included in a radiation image can be estimated.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. A radiation imaging apparatus, comprising:
a generating unit configured to generate a material characteristic image using a plurality of radiation images of different radiation energy levels captured by a radiation detection apparatus;
a calculation unit configured to calculate evaluation information indicating a correlation between a plurality of material characteristic images; and
an estimation unit configured to estimate an amount of scattered rays included in the plurality of radiation images based on the evaluation information.

2. The radiation imaging apparatus according to claim 1, wherein the estimation unit generates image information obtained by subtracting a set amount of scattered rays from the radiation image, and the calculation unit calculates the evaluation information based on the image information.

3. The radiation imaging apparatus according to claim 2, wherein the estimation unit generates image information obtained by changing the setting of the amount of scattered rays, and
the calculation unit repetitively calculates the evaluation information based on the image information generated by the amount of scattered rays with the changed setting.

4. The radiation imaging apparatus according to claim 1, wherein the calculation unit is configured to determine whether the evaluation information obtained by repetitive calculation has converged, and
when the evaluation information has converged, the estimation unit estimates an amount of scattered rays used to calculate the converged evaluation information as the amount of scattered rays included in the plurality of radiation images.

5. The radiation imaging apparatus according to claim 1, wherein the generating unit is configured to generate an image of an effective atomic number of a material that forms an object or material separation images separated according to respective materials forming the object as the material characteristic image.

6. The radiation imaging apparatus according to claim 5, wherein the generating unit is configured to generate a material separation image in which a thickness of the material is corrected based on the estimated amount of scattered rays.

7. The radiation imaging apparatus according to claim 1, wherein the estimation unit is configured to use a function having pixel value dependence representing a distribution shape of the amount of scattered rays, and
to generate image information by subtracting the amount of scattered rays represented by the function from the radiation image.

8. The radiation imaging apparatus according to claim 1, wherein the estimation unit is configured to use a function having positional dependence representing a distribution shape of the amount of scattered rays, and
to generate image information by subtracting the amount of scattered rays represented by the function from the radiation image.

9. The radiation imaging apparatus according to claim 1, wherein the estimation unit is configured to use a function having object imaging part dependence representing a distribution shape of the amount of scattered rays, and
to generate image information by subtracting the amount of scattered rays represented by the function from the radiation image.

10. The radiation imaging apparatus according to claim 7, wherein the calculation unit is configured to calculate the evaluation information based on the image information, and
to repetitively calculate the evaluation information based on image information generated by an amount of scattered rays in which a value of the function has changed.

11. The radiation imaging apparatus according to claim 1, wherein the calculation unit is configured to calculate a correlation coefficient indicating a correlation between the plurality of material characteristic images as the evaluation information.

12. The radiation imaging apparatus according to claim 11, wherein the estimation unit is configured to estimate an amount of scattered rays at which an absolute value of correlation coefficient becomes minimum as the amount of scattered rays included in the plurality of radiation images when the calculation unit calculates the correlation coefficient as the evaluation information.

13. The radiation imaging apparatus according to claim 1, wherein the calculation unit is configured to calculate mutual information, information entropy, sum of absolute differences or sum of squared differences as the evaluation information that indicates a correlation between the plurality of material characteristic images.

14. The radiation imaging apparatus according to claim 13, wherein the estimation unit is configured to estimate an amount of scattered rays at which a result of the calculation becomes maximum as the amount of scattered rays included in the plurality of radiation images.

15. The radiation imaging apparatus according to claim 1, further comprising an obtainment unit configured to obtain a plurality of radiation images captured by the radiation detection apparatus based on a single radiation irradiation operation performed from a radiation generating unit.

16. The radiation imaging apparatus according to claim 15, wherein the obtainment unit is configured to obtain a plurality of radiation images captured by the radiation detection apparatus as the plurality of radiation images based on different radiation energy levels, and the generating unit is configured to generate the plurality of material characteristic images based on the plurality of radiation images obtained by the obtainment unit.

17. The radiation imaging apparatus according to claim 1, further comprising:

a display control unit configured to cause a display unit to display a captured radiation image; and the display control unit is further configured to display a combined radiation image including an amount of scattered rays, a radiation image obtained by subtracting the amount of scattered rays from the radiation image, or material separation images based on thicknesses of respective separated materials.

18. The radiation imaging apparatus according to claim 17, wherein the display control unit is configured to cause the display unit to display at least one image displayed on the display unit.

19. A radiation imaging method, comprising the steps of:

generating, by an image processing unit, a material characteristic image using a plurality of radiation images using a plurality of radiation images of different radiation energy levels captured by a radiation detection apparatus;

calculating, by the image processing unit, evaluation information that correlates between a plurality of material characteristic images; and estimating, by the image processing unit, an amount of scattered rays included in the plurality of radiation images based on the evaluation information.

20. A non-transitory computer-readable storage medium storing a program for causing a computer to execute each step of the radiation imaging method defined in claim 19.

* * * * *